(12) United States Patent
Takahashi et al.

(10) Patent No.: US 6,867,285 B2
(45) Date of Patent: Mar. 15, 2005

(54) VIRUS-FREE PLASMA PROTEIN COMPOSITIONS TREATED WITH POROUS MEMBRANE AND PROCESS FOR PRODUCING THE SAME

(75) Inventors: Tsuyoshi Takahashi, Tokyo (JP); Koji Furushima, Tokyo (JP); Masanori Morita, Tokyo (JP); Muneo Tsujikawa, Tokyo (JP); Takeru Urayama, Tokyo (JP); Nobuaki Hamato, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 44 days.

(21) Appl. No.: 10/168,180

(22) PCT Filed: Dec. 20, 2000

(86) PCT No.: PCT/JP00/09057

§ 371 (c)(1),
(2), (4) Date: Jul. 15, 2002

(87) PCT Pub. No.: WO01/45719

PCT Pub. Date: Jun. 28, 2001

(65) Prior Publication Data

US 2003/0069399 A1 Apr. 10, 2003

(30) Foreign Application Priority Data

Dec. 20, 1999 (JP) ............................................ 11-360950

(51) Int. Cl.$^7$ .......................... C07K 1/00; C07K 14/00; A61K 35/14
(52) U.S. Cl. ............................. 530/382; 530/380; 514/2
(58) Field of Search ............................. 514/2; 530/380, 530/382; 422/31

(56) References Cited

U.S. PATENT DOCUMENTS

| 4,543,210 A | | 9/1985 | Mitra et al. ................. 530/383 |
| 5,817,765 A | * | 10/1998 | Isaksson et al. ............ 530/364 |
| 6,096,872 A | * | 8/2000 | Van Holten et al. ..... 530/390.1 |
| 6,413,714 B1 | * | 7/2002 | Margolis-Nunno et al. .... 435/2 |
| 6,429,192 B1 | * | 8/2002 | Laursen ........................ 514/8 |

FOREIGN PATENT DOCUMENTS

| JP | 1-192368 | 8/1989 |
| JP | 1-254205 | 10/1989 |
| JP | 10-506607 | 6/1998 |

OTHER PUBLICATIONS

Burnouf, T. and Radosevich, M. Haemophilia 9(1): 24–37 Jan. 2003.*
Alsono-Rubiano, E. et al. Haemophilia 9(1): 110–115 Jan. 2003.*

* cited by examiner

Primary Examiner—Jon Weber
Assistant Examiner—Anand Desai
(74) Attorney, Agent, or Firm—Wenderoth, Lind & Ponack, L.L.P.

(57) ABSTRACT

Contaminant viruses can be efficiently removed almost without losing the activity of protein by subjecting a plasma protein composition having a high risk of viral contamination to a treatment with a porous membrane having a pore size greater than a single-particle size of the virus, particularly by subjecting a plasma protein composition to a fractionation treatment by precipitation, before the porous membrane treatment. Particularly, a fibrinogen composition substantially free of non-enveloped viruses, Parvovirus among others, can be provided. By the application of the present invention, a safe plasma protein preparation free of viruses can be conveniently provided.

8 Claims, No Drawings

VIRUS-FREE PLASMA PROTEIN COMPOSITIONS TREATED WITH POROUS MEMBRANE AND PROCESS FOR PRODUCING THE SAME

This application is a 371 of PCT/JP00/09057 filed Dec. 20, 2000.

TECHNICAL FIELD

The present invention relates to a process for producing a plasma protein composition free of viruses, particularly infectious viruses, in the plasma protein composition, a plasma protein composition substantially free of viruses, particularly infectious viruses, which is obtained by this method, a fibrinogen composition substantially free of non-enveloped viruses, particularly Parvovirus and/or hepatitis A virus, and to a method for removing viruses in a plasma protein composition.

BACKGROUND ART

There is the possibility that protein preparations, particularly plasma fractionation preparations prepared from human plasma as a starting material, may be contaminated with pathogen capable of infecting human, and the problem of viral infection is therefore particularly significant. To date, we have had incidents of viral infection with human immunodeficiency virus (HIV), hepatitis A virus (HAV), hepatitis B virus (HBV), hepatitis C virus (HCV) and the like, due to transfusion.

These are not incidents in the past. While the frequency of the incidence is strikingly decreasing by exponential numbers after the introduction of a number of techniques, the occurrence of the incident cannot be completely denied even at present.

To prevent propagation of these viruses, various methods are known that inactivate or remove possibly contaminant viruses. For example, a method of heating a protein-containing composition in a liquid state (JP-A-55-145615, JP-A-56-139422, JP-A-56-106594 and the like), a method of heating in a dry state (Japanese Patent Application under PCT laid-open under kohyo No. 58-500548, JP-A-58-213721 and the like), a method comprising contact with trialkylphosphate and/or a surfactant and the like (JP-A-60-51116 and the like), a method comprising UV irradiation (JP-A-7-196531 and the like), a method comprising virus removal membrane (JP-A-9-100239 and the like), and the like are known.

However, every single treatment to inactivate or remove viruses is associated with difficulty in completely inactivating or removing contaminant viruses without losing the protein activity, because the heat treatment leaves viruses highly resistant to heat, the surfactant treatment leaves non-enveloped viruses, and the treatment exclusively by irradiation possibly deactivates protein and the like.

Thus, the above-mentioned methods for inactivating or removing contaminant viruses are currently used in suitable combinations for this purpose.

Fibrinogen is obtained from a fraction first precipitated during the process of alcohol plasma fractionation. Therefore, it is susceptible to the consequence of contamination once a virus invades plasma. Parvovirus B19 (hereinafter B19) is particularly drawing much attention lately. This virus does not have an envelope, is resistant to heat and has an extremely small single-particle size of about 18–25 nm, due to which properties its inactivation/removal is desired and is being investigated particularly in the field of plasma fractionation preparation.

A method using a virus removal membrane is naturally capable of removing viruses having a greater molecule size than its pore size upon filtration, but otherwise when the virus is smaller in size than the pore size. In addition, the use of a removal membrane having too small a pore size results in clogging with a sample and the like, which makes filtration itself difficult. Furthermore, lower flow rates in parallel with the sample amounts during a membrane treatment give rise to many problems such as limited sample amount to be treated and a longer treatment time.

Particularly, when a currently commercially available porous membrane having a membrane pore size of less than 35 nm was used for purification of fibrinogen, the above-mentioned problems of clogging, limited sample amount to be treated and longer treatment time actually occurred due to the molecular weight of fibrinogen and the like. Consequently, only a porous membrane having a membrane pore size of not less than 35 nm can be used. As mentioned above, Parvovirus (B19) has a single-particle size of about 18–25. nm Accordingly, the virus cannot be removed by a sole use of PLANOVA 35 N or PLANOVA 75N (both trademarks, now commercially available porous membrane having a pore size of 35 nm or 75 nm, manufactured by Asahi Kasei Corporation), or even by a method using these virus removal membranes in multi-steps.

Therefore, there has been a demand for a method capable of providing a less virus-infectious and safe protein preparation by a convenient treatment method.

DISCLOSURE OF THE INVENTION

The present inventors have conducted intensive studies in an attempt to solve these problems, and found that a porous membrane treatment affords efficient removal of contaminant viruses almost without losing the activity of protein, which resulted in the completion of the present invention. The present inventors have further found that a porous membrane treatment affords a fibrinogen composition substantially free of non-enveloped viruses, particularly Parvovirus and/or hepatitis A virus, which resulted in the completion of the present invention.

Accordingly, the present invention provides the following.

(1) A production method of a plasma protein composition free of viruses, which comprises subjecting the plasma protein composition to a treatment with a porous membrane having a pore size greater than a single-particle size of the virus.
(2) The production method according to the aforementioned (1), wherein the porous membrane is a porous hollow fiber membrane.
(3) The production method according to the aforementioned (1) or (2), wherein the plasma protein composition is subjected to a fractionation treatment by precipitation, before the porous membrane treatment.
(4) The production method according to any of the aforementioned (1) to (3), wherein the plasma protein composition is subjected to a fractionation treatment by precipitation and the obtained precipitate is extracted with water, before the porous membrane treatment.
(5) The production method according to any of the aforementioned (1) to (4), wherein the plasma protein composition contains at least one kind of protein selected from the group consisting of fibronectin, fibrinogen, coagulation factor V, coagulation factor VIII, von Willebrand Factor, coagulation factor XIII, retinol binding protein, α-globulin, β-globulin and γ-globulin.

(6) The production method according to the aforementioned (5), wherein the plasma protein composition contains at least fibrinogen.

(7) The production method according to any of the aforementioned (1) to (6), wherein the virus is a non-enveloped virus.

(8) The production method according to the aforementioned (7), wherein the non-enveloped virus is Parvovirus and/or hepatitis A virus.

(9) A plasma protein composition substantially free of a virus as a result of a treatment with a porous membrane having a pore size greater than a single-particle size of the virus.

(10) The plasma protein composition according to the aforementioned (9), wherein the porous membrane is a porous hollow fiber membrane.

(11) The plasma protein composition according to the aforementioned (9) or (10), wherein the plasma protein composition is subjected to a fractionation treatment by precipitation, before a porous membrane treatment.

(12) The plasma protein composition according to any of the aforementioned (9) to (11), wherein the plasma protein composition is subjected to a fractionation treatment by precipitation and the obtained precipitate is extracted with water, before the porous membrane treatment.

(13) The plasma protein composition according to any of the aforementioned (9) to (12), wherein the plasma protein composition contains at least one kind of protein selected from the group consisting of fibronectin, fibrinogen, coagulation factor V, coagulation factor VIII, von Willebrand Factor, coagulation factor XIII, retinol binding protein, α-globulin, β-globulin and γ-globulin.

(14) The plasma protein composition according to the aforementioned (13), wherein the plasma protein composition contains at least fibrinogen.

(15) The plasma protein composition according to any of the aforementioned (9) to (14), wherein the virus is a non-enveloped virus.

(16) The plasma protein composition according to the aforementioned (15), wherein the non-enveloped virus is Parvovirus and/or hepatitis A virus.

(17) A fibrinogen composition substantially free of Parvovirus.

(18) A method for removing virus in a plasma protein composition, which comprises subjecting the plasma protein composition to a treatment with a porous membrane having a pore size greater than a single-particle size of the virus.

(19) The method according to the aforementioned (18), wherein the porous membrane is a porous hollow fiber membrane.

(20) The method according to the aforementioned (18) or (19), wherein the plasma protein composition is subjected to a fractionation treatment by precipitation, before the porous membrane treatment.

(21) The method according to any of the aforementioned (18) to (20), wherein the plasma protein composition is subjected to a fractionation treatment by precipitation and the obtained precipitate is extracted with water, before the porous membrane treatment.

In the present invention, the plasma protein in the plasma protein composition is not particularly limited and may be any as long as it is contained in blood. For example, the plasma protein particularly capable of achieving the expected effect according to the method of the present invention has a high molecular weight and has a high risk of viral contamination. Examples thereof include fibronectin, fibrinogen, coagulation factor V, coagulation factor VIII, von Willebrand Factor, coagulation factor XIII, retinol binding protein, α-globulin, β-globulin and γ-globulin and the like. Particularly, since fibrinogen is obtained from a fraction first precipitated during the process of alcohol plasma fractionation, it is susceptible to viral contamination when a virus is mixed in plasma. Thus, removal of non-enveloped viruses by the convenient method of the present invention is useful.

The plasma protein composition subject to the method of the present invention is free of any particular limitation as long as its viral contamination, particularly with infectious virus, is feared and a composition can be subjected to a porous membrane treatment. The composition is generally liquid, such as a solution containing fractions obtained from, for example, plasma or tissue extract by treatment according to various fractionation methods, culture liquid obtained by culture of genetically recombined host or tissue, commercially available protein preparation and the like.

The purification level is not particularly limited and the composition may be of any purification level. The purification level may be achieved by appropriately selecting and utilizing general purification methods, such as PEG (polyethylene glycol) fractionation, alcohol fractionation, glycine fractionation, gel filtration, ion exchange chromatography, affinity chromatography, hydrophobic chromatography and the like.

The precipitation method includes those known per se as protein fractionation methods. Examples thereof include precipitation methods using neutral salts (the precipitation method using the salts is what is called a salting-out method using sulfate, sulfite, thiosulfate, phosphate, alkali metal salt, ammonia, magnesium, halogen compound and the like), water-soluble organic solvents (e.g., ethanol, methanol, ethyl ether, acetone etc.), water-soluble non-ionized polymer compounds (e.g., polyethylene glycol (PEG), dextran, polyvinylpyrrolidone (PVP), nonylphenolethoxylate etc.), metal ions (e.g., barium sulfate, aluminum hydroxide etc.), organic cations (rivanol, protamine, other cationic surfactants etc.), anions (e.g., low molecular anion such as picric acid, trichloroacetic acid, sulfosalicylic acid, perchloric acid and the like, polyanion such as polyacrylic acid, polystyrene sulfonate, polyphosphate and the like), and the like, precipitation method by desalting (dialysis, dilution method etc.), glycine precipitation method (glycine-sodium chloride precipitation method), and the like.

The precipitation method used in the present invention is one similar to the method used for general protein fractionation treatment, wherein similar conditions are employed. Each substance used for the precipitation method of the present invention can be determined as appropriate according to the solubility of the objective protein to be separated. For example, one capable of affording the objective protein as a precipitate by changing the surface charge and hydrophilicity of the protein molecule, or one capable of precipitating unnecessary proteins to afford the objective protein in a supernatant can be used, wherein the conditions of the precipitation treatment may be determined as appropriate according to respective proteins. Thus, various factors influential on the precipitation method, such as hydrogen ion concentration or pH, ionic strength, dielectric constant, temperature, protein concentration, other ions and the like, can be determined according to the objective protein. The conditions of use thereof can be also determined according to the objective protein.

Particularly, when the protein is fibrinogen, glycine precipitation method is preferable, and glycine-sodium chloride precipitation method is more preferable. The concentration of glycine is not lower than 50 g/L, preferably not lower than 75 g/L, and that of sodium chloride is 10 g/L, preferably not lower than 30 g/L. The upper limit is 250 g/L, preferably 225 g/L, for glycine, and 175 g/L, preferably 150 g/L, for sodium chloride.

The respective proteins separated by the above-mentioned precipitation methods are subjected to typical centrifugation treatment and various filtration steps to give necessary fractions.

When the objective protein is obtained as a precipitate, it requires extraction with and dissolution in a suitable solvent for subsequent purification. The solvent is free of any particular limitation, and solvents, buffers and the like generally used for purification of protein can be used. When the protein is fibrinogen, citrate buffer solution and water are generally used for extraction and dissolution. Particularly, typical centrifugation or clarifying filtration step after extraction with water enhances the effect provided by the present invention.

In the present invention, a porous membrane treatment refers to a filtration of plasma protein associated with the risk of virus contamination, through a porous membrane.

The material of the porous membrane to be used in the present invention is not particularly limited and synthetic polymer compounds such as regenerated cellulose, cellulose acetate, polyvinylidene fluoride, polyethersulfone, polyacrylonitrile, polysulfone, polymethyl methacrylate and the like can be used. Preferred is regenerated cellulose.

The form of the membrane may be a hollow fiber, a sheet and the like, which is preferably a hollow fiber. For example, a porous hollow fiber membrane made of regenerated cellulose can be prepared from a cupric ammonium solution of cellulose by a micro-phase separation method [Am. Chem. Soc., 9, 197–228 (1985)].

While the average pore size of the porous membrane to be used varies depending on the kind of protein and the kind of virus to be removed, it is generally 1–100 nm, preferably 10–100 nm. The pore size is 35–100 nm, preferably 35–75 nm, particularly when Parvovirus, HAV and the like are to be removed from a protein having a high molecular weight, such as fibrinogen and the like.

When the porous membrane is a hollow fiber, the membrane is preferably in the form of a module. For example, a number of porous hollow fiber membranes are bundled in parallel, fit in a cartridge and integrated with an adhesive to give a module.

Usable commercially available membranes include PLANOVA series (trademark, manufactured by Asahi Kasei Corporation) having a multilayer structure comprising more than 100 layers of peripheral walls to be the membrane, VIRESOLVE series (trademarks, manufactured by Millipore Corporation) known as a virus removal membrane, OMEGA VR series (trademark, manufactured by Pall Corporation), ULTIPOR series (trademark, manufactured by Pall Corporation) and the like. Particularly preferred are PLANOVA series.

The temperature at which the plasma protein composition is treated with or filtered through a porous membrane is 4–50° C., preferably 4–37° C.

The filtration pressure is 10–100 kpa, preferably 10–90 kpa. The method of filtration includes crossflow filtration (circulation method), wherein the solution is filtered under a strain rate, and dead-end filtration (non-circulation method), wherein the solution is filtered without a strain rate. Preferred is dead-end filtration using pressurized air and the like.

During filtration through a porous membrane, chaotropic ion or amino acid may be added to a sample. This allows enhanced expression of the effect of the present invention that contaminant viruses can be removed efficiently by a porous membrane treatment almost without losing the activity of protein.

The kind of the chaotropic ion or amino acid in this case is not particularly limited and those generally used for purification of proteins can be used. Particularly, chlorine ion, arginine and the like are preferable.

This filtration treatment may be applied once or more than once. Repeat treatment affords more superior virus removal effect upon filtration.

Particularly, the present invention treats a plasma protein composition with a porous membrane having a pore size greater than a single-particle size of the virus, whereby viruses having a single-particle size smaller than the pore size of a porous membrane can be removed. As a result, the plasma protein composition substantially free of the virus can be obtained.

When the virus is a single-particle, by the "porous membrane having a pore size greater than a single-particle size of the virus" is meant a porous membrane that permits passage of the virus.

According to the present invention, therefore, contaminant viruses can be removed efficiently almost without losing the activity of protein, and a plasma protein composition as a starting material of a safer plasma protein preparation can be provided.

Specific examples of the virus removed by the method of the present invention include vaccinia virus, mumps virus, herpes simplex virus, ECHO virus, Parvovirus, HIV, HAV, HBV, HCV, TTV and the like. Particularly, examples of the non-enveloped virus associated with the risk of contamination include Parvovirus, HAV and the like.

The plasma protein composition thus obtained can be used as it is, or is purified by a conventional protein purification method, such as PEG (polyethylene glycol) fractionation, alcohol fractionation, glycine fractionation, gel filtration, ion exchange chromatography, affinity chromatography, hydrophobic chromatography and the like and used as a plasma protein preparation.

The plasma protein preparation is formed into a liquid preparation or dry preparation by a conventional method, which may contain, where necessary, a typical pharmacologically acceptable additive for a pharmaceutical agent, such as antiseptic, antibacterial, chelating agent, thickener, isotonizing agent and the like, or pharmaceutically necessary components.

The production method of the present invention produces a plasma protein composition substantially free of viruses. The virus inactivation or removal methods generally employed, such as dry heating, liquid heating, surfactant treatment, UV irradiation treatment, virus removal membrane treatment and the like, may be combined as appropriate before and after the method of the present invention, whereby the inactivation or removal of the virus can be made more complete.

In the present invention, by the "substantially free of virus" is meant being below the detection limit by a known virus measurement method.

EXAMPLES

The present invention is explained in more detail in the following by way of Experimental Examples, Reference Examples and the like, which are not to be construed as limitative.

Example 1

Cohn's Fr. I fraction (100 g) derived from normal human plasma was dissolved in 1.5 L of citrate buffer solution and tri-(n-butyl)phosphate (TNBP) was added to 0.3 w/v % and TWEEN 80 was added to 1 w/v %. A surfactant treatment was conducted at 30° C. for 6 hr.

Parvovirus ($10^{2.7}$ copies/mL) was added as a monitor virus to the sample after the surfactant treatment.

This sample was subjected to a fractionation treatment by precipitation using 15% glycine-1M sodium chloride, and fibrinogen was precipitated by centrifugation (4,000 rpm, 20 min) and recovered. The recovered fibrinogen was dissolved in 1.0 L of citrate buffer solution to give a 1.0% solution. This solution was used as a sample before filtration and its virus amount was measured.

This solution was subjected to a dead-end filtration using PLANOVA 75N (average pore size 72±4 nm) at a temperature of 23° C. and a filtration pressure of 10 kpa to remove viruses. The filtrate was used as a sample after filtration and its virus amount was measured.

Example 2

Cohn's Fr. I fraction (100 g) derived from normal human plasma was dissolved in 1.5 L of citrate buffer solution and tri-(n-butyl)phosphate (TNBP) was added to 0.3 w/v % and TWEEN 80 was added to 1 w/v %. A surfactant treatment was conducted at 30° C. for 6 hr.

This sample was subjected to a fractionation treatment by precipitation using 15% glycine-1M sodium chloride, and fibrinogen was precipitated by centrifugation (4,000 rpm, 20 min) and recovered. The recovered fibrinogen was dissolved in 1.0 L of citrate buffer solution to give a 1.0% solution.

Parvovirus ($10^{5.7}$ copies/mL) was added as a monitor virus to this solution.

Thereafter, this sample was subjected to a fractionation treatment using 15% glycine-1M sodium chloride, and fibrinogen was precipitated by centrifugation (4,000 rpm, 20 min) and recovered. The recovered fibrinogen was dissolved in 1.0 L of citrate buffer solution to give a 1.0% solution. This solution was used as a sample before filtration and its virus amount was measured.

The obtained solution was subjected to a dead-end filtration suing PLANOVA 75N (average pore size 72±4 nm) at a temperature of 23° C. and a filtration pressure of 10 kpa to remove viruses. The filtrate was used as a sample after filtration and its virus amount was measured.

Example 3

Cohn's Fr. I fraction (100 g) derived from normal human plasma was dissolved in 1.5 L of physiological saline and tri-(n-butyl) phosphate (TNBP) was added to 0.3 w/v % and TWEEN 80 was added to 1 w/v %. A surfactant treatment was conducted at 30° C. for 6 hr.

Parvovirus was added as a monitor virus to the sample after the surfactant treatment.

This sample was subjected to a fractionation treatment by precipitation using 15% glycine-1M sodium chloride, and fibrinogen was precipitated by centrifugation (4,000 rpm, 20 min) and recovered. The recovered fibrinogen was dissolved in 1.0 L of citrate buffer solution to give a 1.0% solution. This solution was used as a sample before filtration and its virus amount was measured. In addition, this solution was taken as a sample before filtration and absorbance at 280 nm was measured to determine its protein amount.

This solution was subjected to a dead-end filtration using PLANOVA 75N (average pore size 72±4 nm) at a temperature of 23° C. and a filtration pressure of 10 kpa to remove viruses. The filtrate was used as a sample after filtration and its virus amount was measured. In addition, absorbance at 280 nm was measured to determine its protein amount.

This filtrate was subjected to a dead-end filtration using PLANOVA 35N (average pore size 35±2 nm) at a temperature of 23° C. and a filtration pressure of 10 kpa to remove viruses. The filtrate was used as a sample after filtration and its virus amount was measured. In addition, absorbance at 280 nm was measured to determine the protein amount of this filtrate.

In this case, by filtration combining PLANOVA 75N and PLANOVA 35N, a virus removal effect of not less than $10^6$ copies/mL was shown before and after the filtration.

Example 4

Cohn's Fr. I fraction (100 g) derived from normal human plasma was dissolved in 1.5 L of physiological saline and tri-(n-butyl)phosphate (TNBP) was added to 0.3 w/v % and TWEEN 80 was added to 1 w/v %. A surfactant treatment was conducted at 30° C. for 6 hr.

Parvovirus ($10^{10.1}$ copies/mL) was added as a monitor virus to the sample after the surfactant treatment.

This sample was subjected to a fractionation treatment by precipitation using 8% glycine-1M sodium chloride, and fibrinogen was precipitated by centrifugation (4,000 rpm, 20 min) and recovered. The recovered fibrinogen was dissolved in 1.5 L of water for injection to give a fibrinogen solution. The insoluble material in this solution was removed by a centrifugation treatment and sodium chloride (0.9 g/L) was added. This solution was used as a sample before filtration.

This solution was subjected to a dead-end filtration using PLANOVA 35N (average pore size 35±2 nm) at a temperature of 23° C. and a filtration pressure of 10 kpa to remove viruses. The filtrate was used as a sample after filtration and its virus amount was measured.

In this case, as a result of the treatment combining glycine-sodium chloride fractionation, water extraction of precipitate, centrifugal removal and PLANOVA 35N, a virus removal effect of not less than $10^6$ copies/mL was shown before and after filtration.

Cohn's Fr. I fraction (100 g) derived from normal human plasma was dissolved in 1.5 L of physiological saline and tri-(n-butyl)phosphate (TNBP) was added to 0.3 w/v % and TWEEN 80 was added to 1 w/v %. A surfactant treatment was conducted at 30° C. for 6 hr.

EMC ($10^{8.4}$ TCID$_{50}$/ml) was added as a monitor virus to the sample after the surfactant treatment.

This sample was subjected to a fractionation treatment by precipitation using 8% glycine-1M sodium chloride, and fibrinogen was precipitated by centrifugation (4,000 rpm, 20 min) and recovered. The recovered fibrinogen was dissolved in 1.5 L of water for injection to give a fibrinogen solution. The insoluble material in this solution was removed by a centrifugation treatment and sodium chloride (0.9 g/L) was added. This solution was used as a sample before filtration.

This solution was subjected to a dead-end filtration using PLANOVA 35N (average pore size 35±2 nm) at a temperature of 23° C. and a filtration pressure of 10 kpa to remove viruses. The filtrate was used as a sample after filtration and its virus amount was measured.

In this case, as a result of the treatment combining a fractionation treatment by precipitation using glycine-sodium chloride, water extraction of precipitate, centrifugal removal and PLANOVA 35N, a virus removal effect of not less than $10^4$ TCID$_{50}$/ml was shown before and after the treatment.

Reference Example 1

Cohn's Fr I fraction (110 g) derived from normal human plasma was dissolved in 1.5 L of physiological saline and TNBP was added to 0.3 w/v% TWEEN 80 was added to 1 w/v%. A surfactant treament was conducted at 30° C. for 6 hr.

This sample was subjected to a fractionation treatment by precipitation using 15% glycine-1M sodium chloride, and fibrinogen was precipitated and recovered. The recovered fibrinogen was dissolved in 1.0 L of citrate buffer solution to give a 1.0% solution.

Parvovirus ($10^{10.7}$ copies/mL) was added as a monitor virus to this solution.

This solution was used as a sample before filtration and its virus amount was measured.

This solution was subjected to a dead-end filtration using PLANOVA 75N (average pore size 72±4 nm) at a temperature of 23° C. and a filtration pressure of 10 kpa to remove viruses. The filtrate was used as a sample after filtration and its virus amount was measured.

Reference Example 2

In the same manner as in Reference Example 1 except that Parvovirus ($10^{11.7}$ copies/mL) was added as a monitor virus and the solution was subjected to a dead-end filtration using Planova 35N (average pore size 35±2 nm) at a temperature of 23° C. and a filtration pressure of 10 kpa, the virus amount of each sample was measured.

Reference Example 3

Cohn's Fr. I fraction (100 g) derived from normal human plasma was dissolved in 1.5 L of physiological saline and tri-(n-butyl) phosphate (TNBP) was added to 0.3 w/v % and TWEEN 80 was added to 1 w/v %. A surfactant treatment was conducted at 30° C. for 6 hr.

This sample was subjected to a fractionation treatment by precipitation using 15% glycine-1M sodium chloride, and fibrinogen was precipitated and recovered. The recovered fibrinogen was dissolved in 1.0 L of citrate buffer solution to give a 1.0% solution.

Parvovirus ($10^{5.7}$ copies/mL) was added as a monitor virus to this solution.

This solution was subjected to a dead-end filtration using PLANOVA 75N (average pore size 72±4 nm) at a temperature of 23° C. and a filtration pressure of 10 kpa to remove viruses. The filtrate was used as a sample after filtration and its virus amount was measured.

This filtrate was subjected to a dead-end filtration using PLANOVA 35 N (average pore size 35±2 nm) at a temperature of 23° C. and a filtration pressure of 10 kpa to remove viruses. The filtrate was used as a sample after filtration and its virus amount was measured.

Measurement Method of Virus Amount (1) For the measurement of virus amount of Parvovirus, the residual amount of viral nucleic acid in each sample was measured by polymerase chain reaction (PCR) measurement (Transfusion Vol. 32, p. 824–828 (1992)). The nucleic acid amount of Parvovirus in an amount of $10^2$ copies/mL falls below detection limit.

(2) EMC virus (encephalomyocarditis virus) was evaluated by measurement of infectivity titer (TCID$_{50}$) using Vero cells.

The infectivity titer of EMC virus for Vero cells falls below detection limit at $10^{1.5}$ TCID$_{50}$/ml.

The results of the above-mentioned Examples 1–2, 4–5 and Reference Examples 1–3 are shown in Table 1.

Measurement Method of Protein Amount

Respective samples were appropriately diluted with physiological saline and absorbance at 280 nm was measured. The results of the above-mentioned Example 3 are shown in Table 2.

TABLE 1

| | | Porous membrane filter (pore size) | Virus amount | | | |
|---|---|---|---|---|---|---|
| | | | 75 nm | | 35 nm | |
| | Pre-treatment | | before filtration (added) | after filtration | before filtration (added) | after filtration |
| Ex. 1 | glycine - sodium chloride | 75 nm | $10^{2.7}$ | below detection limit (Parvo B19: copies/mL) | — | — |
| Ex. 2 | glycine - sodium chloride | 75 nm | $10^{5.7}$ | below detection limit (Parvo B19: copies/mL) | — | — |
| Ex. 4 | glycine - sodium chloride + water extraction | 35 nm | — | — | $10^{10.1}$ | below detection limit (Parvo B19: copies/mL) |
| Ex. 5 | glycine - sodium chloride + water extraction | 35 nm | — | — | $10^{8.4}$ | below detection limit (EMC:TCID$_{50}$/mL) |
| Ref. Ex. 1 | none | 75 nm | $10^{10.7}$ | $10^{10.7}$ | — | — |
| Ref. Ex. 2 | none | 35 nm | — | — | $10^{11.7}$ | $10^{11.7}$ |
| Ref. Ex. 3 | none | 75 nm + 35 nm | $10^{5.7}$ | $10^{5.7}$ | $10^{5.7}$ | $10^{5.7}$ |

(Parvo B19: copies/mL)

TABLE 2

| | | Absorbance at 280 nm | | | |
|---|---|---|---|---|---|
| | | 75 nm | | 35 nm | |
| | Pre-treatment | Porous membrane filter (pore size) | before filtration | after filtration | before filtration | after filtration |
| Ex. 3 | glycine - sodium chloride | 75 nm + 35 nm | 10.4 | 10.2 | 10.2 | 10.0 |

INDUSTRIAL APPLICABILITY

According to the present invention, by subjecting a plasma protein composition to a porous membrane treatment, contaminant viruses in the plasma protein can be removed efficiently almost without losing the activity of protein. Accordingly, the present invention provides a plasma protein free of a risk of viral infection. Particularly, by the porous membrane treatment of the present invention, a fibrinogen composition substantially free of non-enveloped viruses, Parvovirus and/or hepatitis A virus among others, can be provided.

This application is based on patent application No. 360950/1999 filed in Japan, the contents of which are hereby incorporated by reference.

What is claimed is:

1. A production method for producing a plasma protein composition containing fibrinogen free of detectable virus, which comprises:

subjecting the plasma protein composition containing fibrinogen to a fractionation treatment by precipitation to obtain a precipitate;

extracting the precipitate with water; and subjecting the extracted precipitate to a treatment with a porous membrane having a pore size greater than a single-particle size of the virus, wherein the average pore size is 35±2 nm and wherein the virus is parvovirus or encephalomyocarditis virus to produce the plasma protein composition free of detectable virus.

2. The production method according to claim 1, wherein porous membrane is a porous hollow fiber membrane.

3. A method for removing detectable virus in plasma protein composition containing fibrinogen, which comprises:

subjecting the plasma protein composition containing fibrinogen to a fractionation treatment by precipitation to obtain a precipitate;

extracting the precipitate with water; and subjecting the extracted precipitate to a treatment with a porous membrane having a pore size greater than a single-particle size of the virus, wherein the average pore size is 35±2 nm and wherein the virus is parvovirus or encephalomyocarditis virus to produce the plasma protein composition free of detectable virus.

4. The method according to claim 3, wherein the porous membrane is a porous hollow fiber membrane.

5. A method for producing a plasma protein composition comprising fibrinogen free of detectable parvovirus or encephalomyocarditis virus, which comprises:

subjecting the plasma protein composition comprising fibrinogen to a fractionation treatment by precipitation to obtain a precipitate;

subjecting the precipitate to a treatment with a porous membrane having a pore size greater than a single-particle size of the virus, wherein the average pore size is 35±2 nm and the treatment with the porous membrane is conducted a plural number of times to produce the plasma protein composition free of detectable parvovirus or encephalomyocarditis virus.

6. The method according to claim 5, wherein the treatment with the porous membrane is conducted a plural number of times using a porous membrane having a different average pore size.

7. A method for removing detectable parvovirus or encephalomyocarditis virus in a plasma protein composition comprising fibrinogen, which comprises:

subjecting the plasma protein composition comprising fibrinogen to a fractionation treatment by precipitation to obtain a precipitate; and subjecting the precipitate to a treatment with a porous membrane having pore size greater than a single-particle size of the virus, wherein the average pore size is 35±2 nm, and the treatment with the porous membrane is conducted a plural number of times to produce the plasma protein composition free of detectable parvovirus or encephalomyocarditis virus.

8. The method according to claim 7, wherein the treatment with the porous membrane is conducted a plural number of times using a porous membrane having a different average pore size.

* * * * *